US007776795B2

(12) United States Patent
Keeler et al.

(10) Patent No.: US 7,776,795 B2
(45) Date of Patent: *Aug. 17, 2010

(54) IDENTIFICATION, CHARACTERIZATION, AND APPLICATION OF *SHEWANELLA PUTREFACIENS* (LH4:18), USEFUL IN MICROBIALLY ENHANCED OIL RELEASE

(75) Inventors: Sharon Jo Keeler, Bear, DE (US); Edwin R. Hendrickson, Hockessin, DE (US); Linda L. Hnatow, Oxford, PA (US); Scott Christopher Jackson, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 154 days.

This patent is subject to a terminal disclaimer.

(21) Appl. No.: 12/105,690

(22) Filed: Apr. 18, 2008

(65) Prior Publication Data
US 2009/0260803 A1 Oct. 22, 2009

(51) Int. Cl.
*C09K 8/582* (2006.01)
*C12P 39/00* (2006.01)

(52) U.S. Cl. .............. 507/201; 435/42; 435/253.3; 435/281; 435/874

(58) Field of Classification Search ............ 507/201; 435/42, 281, 253.3, 874
See application file for complete search history.

(56) References Cited

U.S. PATENT DOCUMENTS

| 5,877,014 | A | 3/1999 | Shetty et al. | |
|---|---|---|---|---|
| 6,087,155 | A | 7/2000 | York et al. | |
| 6,150,155 | A * | 11/2000 | Wildung et al. | 435/252.1 |
| 6,245,235 | B1 | 6/2001 | Perriello | |
| 6,350,605 | B1 | 2/2002 | Mita et al. | |
| 6,573,087 | B2 | 6/2003 | Lehr | |
| 6,719,902 | B1 | 4/2004 | Alvarez et al. | |
| 6,923,914 | B2 | 8/2005 | Perriello | |
| 2006/0216811 | A1 | 9/2006 | Cunningham et al. | |
| 2007/0092930 | A1 | 4/2007 | Lal et al. | |
| 2009/0263887 | A1* | 10/2009 | Keeler et al. | 435/253.3 |

FOREIGN PATENT DOCUMENTS

WO WO 00/56668 9/2000
WO 0076928 A2 12/2000

OTHER PUBLICATIONS

J. Martín-Gil, *Shewanella putrefaciens* in a Fuel-in-Water Emulsion from the Prestige Oil Spill, Antonie van Leeuwenhoek, 86: 283-285, 2004 (Martin-Gil).*
Burgos et al., Soil Humic Acid Decreases Biological Uranium (VI) Reduction by *Shewanella putrefaciens* CN32, Environ. Eng. Sci., 2007, vol. 24:755-761.
C. Liu et al., Reduction Kinetics of Fe (III), Co (III), U (VI), Cr (VI), and Tc (VII) in Cultures of Dissimilatory Metal-Reducing Bacteria, Biotechnol. Bioeng., 2002, vol. 80:637-649.
R. D. Stapleton Jr., Metal Reduction At Cold Temperatures by *Shewanella* Isolates From Various Marine Environments, Aquat. Microb. Ecol., 2005, vol. 38:81-91.
D. Bagge et al., *Shewanella putrefaciens* Adhesion and Biofilm Formation on Food Processing Surfaces, Appl. Environ. Microbiol., 2001, vol. 67:2319-2325.
Altschul et al., Basic Local Alignment Search Tool, J. Mol. Biol., 1990, vol. 215:403-410.
C. Moreno-Vivian et al., Prokaryotic Nitrate Reduction: Molecular Properties and Functional Distinction Among Bacterial Nitrate Reductases, J. Bacteriol., 1999, vol. 181:6573-6584.
R. D. Fallon et al., Anaerobic Biodegradation of Cyanide Under Methanogenic Conditions, Appl. Environ. Microbiol., 1991, vol. 57:1656-1662.
J. D. Levi et al., MEOR Strategy and Screening Methods for Anaerobic Oil-Mobilizing Bacteria, Intl. Biores. J., 1985, vol. 1:336-344.
Berry et al., In Situ Saturation Measurements Improve Analysis and Interpretation of Laboratory Miscible and Immiscible Displacement Processes, SPE Reservoir Engineering, SPE Paper No. 200056, 1991, pp. 429-436.
M. Saikrishna et al., Development of Bio-Surfactant Based Microbiol Enhanced Oil Recovery Procedure, SPE Paper 89473, 2004, pp. 1-6.
J. L. Bruce, Automated System Rapidly Identifies and Characterizes Microorganisms in Food, Food Technology, 1996, vol. 50:77-81.
M. R. Sethi, Fully Automated Microbiol Characterization and Identification for Industiral Microbiologists, Am. Lab, 1997, vol. 5:31-35.
C. Barbeau et al., Bioremediation of Pentachlorophenol-Contaminated Soil by Bioaugmentation Using Activated Soil, Appl. Microbiol. Biotechnol., 1997, vol. 48:745-752.
Validation of the Publication of New Names and New Combinations Previously Effectively Published Outside the IJSB, Int. J. Syst. Bacteriol., 1986, vol. 36:354-356.
Picardal et al., Involvement of Cytochromes in the Anaerobic Biotransformation of Tetrachloromethane by *Shewanella putrefaciens* 200, Appl. Environ. Microbiol., 1993, vol. 59:3763-3770.
Pearson, William R., Searching Protein Sequence Databases—Is Optimal Best?, Computation Methods in Genome Research (Proc. Intl. Symp. Meeting), 1994, pp. 111-120, Plenum Press, New York.
Labeda, David P., Isolation of Anaerobic Microorganisma, Isolation of Biotechnological Organisms From Nature, 1990, pp. 117-140, McGraw-Hill Publishing Company.
Standard Test Method for Distillation of Crude Petroleum (15-Theoretical Plate Column), Designation: D 2892-05, at ASTM International Standards Worldwide at http://www.Astm.org/D2892.htm, pp. 1-32, Nov. 1, 2005.
Dandekar, Abhijit Y., Petroleum Reservoir Rock and Fluid Properties, 2006, pp. 40-42, Taylor & Francis Group, Boca Raton, Florida.
Standard Test Method for Distillation of Heavy Hydrocarbon Mixtures, Designation D5236-03 at http://www.Astm.org/D5236.htm, pp. 1-18, Dec. 1, 2007.

* cited by examiner

*Primary Examiner*—Timothy J. Kugel

(57) ABSTRACT

The present disclosure relates to isolation, identification and application of *Shewanella putrefaciens* strain LH4:18 that grows, under denitrifying anaerobic conditions, on crude oil as the sole carbon source. This organism assists in oil release from substrate in reservoir simulations when grown on either lactate or peptone as a carbon source. *Shewanella putrefaciens* strain LH4:18 can be used alone or in concert with other microorganisms to improve oil recovery.

17 Claims, 7 Drawing Sheets

Figure 1:
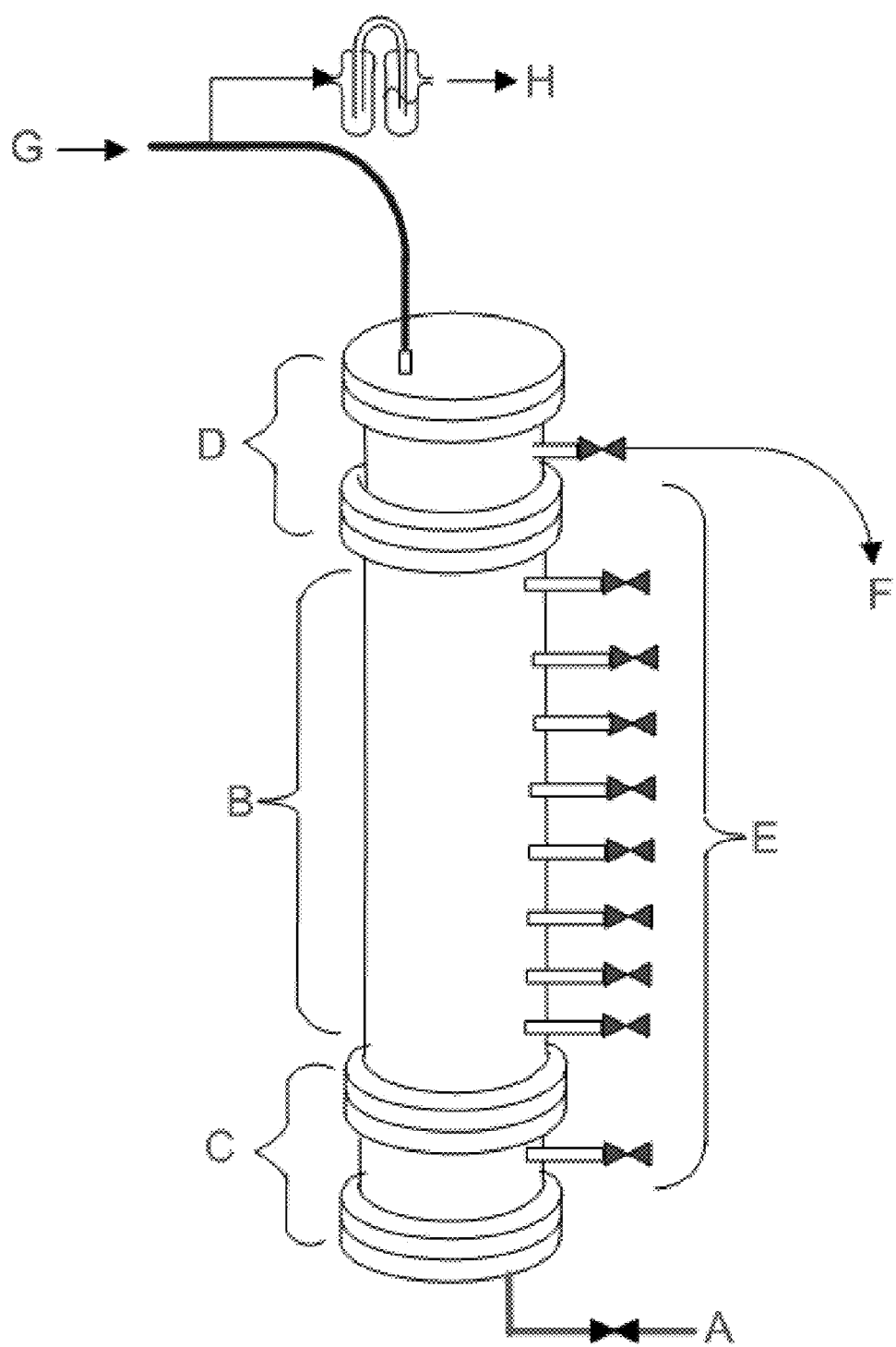

IDENTIFICATION, CHARACTERIZATION, AND APPLICATION OF *SHEWANELLA PUTREFACIENS* (LH4:18), USEFUL IN MICROBIALLY ENHANCED OIL RELEASE

FIELD OF INVENTION

This disclosure relates to the field of environmental microbiology and modification of heavy crude oil properties using microorganisms. More specifically, pure microorganisms are used under denitrifying conditions to modify the properties of heavy crude oil in order to enhance the recovery of the crude oil from its underground reservoir.

BACKGROUND OF THE INVENTION

The challenge to meet the ever increasing demand for oil includes increasing crude oil recovery from heavy oil reservoirs. This challenge has resulted in expanding efforts to develop alternative cost efficient oil recovery processes (Kianipey, S. A. and Donaldson, E. C. $61^{st}$ Annual Technical Conference and Exhibition, New Orleans, La., USA, Oct. 5-8, 1986). Heavy hydrocarbons in the form of petroleum deposits and oil reservoirs are distributed worldwide. These oil reservoirs are measured in the hundreds of billions of recoverable barrels. Because heavy crude oil has a relatively high viscosity, it is essentially immobile and cannot be easily recovered by conventional primary and secondary means.

Microbial Enhanced Oil Recovery (MEOR) is a methodology for increasing oil recovery by the action of microorganisms (Brown, L. R., Vadie, A. A,. Stephen, O. J. SPE 59306, SPE/DOE Improved Oil Recovery Symposium, Oklahoma, Apr. 3-5, 2000). MEOR research and development is an ongoing effort directed at discovering techniques to use microorganisms to modify crude oil properties to benefit oil recovery (Sunde. E., Beeder, J., Nilsen, R. K. Torsvik, T., SPE 24204, SPE/DOE $8^{th}$ Symposium on enhanced Oil Recovery, Tulsa, Okla., USA, Apr. 22-24, 1992).

Methods for identifying microorganisms useful in MEOR processes have been described. These methods require identification of samples drawn from an oil well or reservoir comprising a consortium of microorganisms and enrichment or evolution of populations in the sample under specific conditions with a defined nutrient medium (U.S. Patent Application No. 2007/0092930A1). Thus, there is a need for developing methods to: 1) identify microorganisms that can grow in or on oil under anaerobic denitrifying conditions by selection of pure isolates from enrichment of indigenous microorganisms; 2) screen isolates for properties that might be useful in oil modification or interactions and 3) use said identified microorganisms, in a cost-efficient way, to improve oil recovery.

The organism LH4:18, described herein, was identified by 16S rDNA homology as a strain of *Shewanella putrefaciens*. The 16S rDNA sequence has 100% homology to two of the eight rDNA genes in *Shewanella putrefaciens* strain CN32 and W3-18-1. Both *Shewanella putrefaciens* CN32 (Genome Analysis and System Modeling Group of the Life Sciences Division of Oak Ridge National Laboratory) and *S. putrefaciens* W3-18-1 (DOE Joint Genome Institute) were isolated from environmental samples and have been studied extensively for bioremediation of heavy metals. Strain Conn.32 has been studied by DOE Natural and Accelerated Bioremediation Research group for its ability to reduce polyvalent metals, including iron, manganese, uranium, and chromium (William D. Burgos, W. D., et al., Environ. Eng. Sci., 24, 755-761, 2007; and Liu, C., et al., Biotechnol. Bioeng. 80, 637-649, 2002). Strain W3-18-1 has been studied for remediation of metals and radioactive materials, especially in cold climates (Stapleton Jr., R. D., et al., Aquat. Microb. Ecol. 38:81-91, 2005). Both strains have utility in decreasing solubility of the metals and stabilizing them in situ.

Many *Shewanella putrefaciens* can reduce metal oxides, but there are subtle differences in the ability of each strain implying genetic variability beyond the 16S rDNA homologies. *Shewanella* species are disclosed for remediation of metal contamination (U.S. Pat. No. 6,923,914B2), iron containing mixed waste (U.S. Pat. No. 6,719,902B1), manganese contamination (U.S. Pat. No. 6,350,605B1), and other pollutants with the aide of butane (U.S. Pat. No. 6,245,235B1). In WO00/56668 *Shewanella* species that can utilize butane have been claimed in a method of bioremediation of petroleum contaminants aerobically. In addition, *Shewanella* supplemented with butane was used for reduction of fouling in injection and recovery wells under aerobic conditions (U.S. Pat. No. 6,244,346B1). *Shewanella putrefaciens* is known to produce biofilms (D. Bagge, et al., Appl. Environ. Microbiol., 67, 2319-2325. 2001). Biofilms of *Shewanella* species have potential to sequester gases, in particular $CO_2$, in underground geological formations and prevent their release into the atmosphere (see US20060216811A1). There has been no report to date of *Shewanella* species utilized in enhanced oil recovery.

SUMMARY OF THE INVENTION

The invention relates to the identification of a microorganism from production water samples obtained from an oil reservoir. A screening protocol was developed to identify microbes capable of growth under denitrifying conditions using oil or oil components as the sole source of carbon. These microbes could be grown in situ in an oil reservoir for enhancement of oil recovery. Growth of the microorganisms, and specifically the pure cultures described herein, in an oil well or reservoir enhances economical recovery of oil.

One strain, designated *Shewanella putrefaciens* LH4:18, was identified by 16S rDNA typing as homologous to *Shewanella putrefaciens* (strain CN32). Ribotyping confirmed that the genomic sequences surrounding the 16S and 23 rDNA genes in strain LH4:18 are substantially different compared to other tested *Shewanella putrefaciens* strains and confirmed the uniqueness of *Shewanella putrefaciens* strain LH4:18.

Thus, one aspect relates to an isolated microorganism designated as bacterial isolate *Shewanella putrefaciens* LH4:18 (ATCC No. PTA-8822).

Another aspect relates to an oil recovery enhancing composition comprising: a) *Shewanella putrefaciens* LH4:18 (ATCC No. PTA-8822); b) one or more electron acceptors; and c) at least one carbon source.

A further aspect relates to a method for improving oil recovery from an oil reservoir comprising: a) providing a composition comprising as bacterial isolate *Shewanella putrefaciens* LH4:18 (ATCC No. PTA-8822), and minimal medium comprising simple nitrates capable of promoting the growth of said isolate; and b) inoculating said reservoir with the composition of (a); wherein growth of said isolate, under denitrifying conditions, in the oil reservoir promotes improved oil recovery.

An additional aspect relates to a method for promoting hydrocarbon bioremediation comprising applying bacterial isolate *Shewanella putrefaciens* LH4:18 (ATCC No. PTA-8822) to an area contaminated with hydrocarbons.

Another aspect relates to a method for promoting oil pipeline maintenance comprising applying bacterial isolate *Shewanella putrefaciens* LH4:18 (ATCC No. PTA-8822) to an oil pipeline.

BRIEF DESCRIPTION OF FIGURES AND
SEQUENCES OF THE INVENTION

The following sequences conform with 37 C.F.R. §§1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions. The symbols and format used for nucleotide and amino acid sequence data comply with the rules set forth in 37 C.F.R. §1.822.

```
SEQ ID NO: 1 -   1492R - CGGTTACCTTGTTACGACTT

SEQ ID NO: 2 -   8F - AGAGTTTGATYMTGGCTCAG
```

SEQ ID NOs:1 and 2 were used for amplification of the bacterial rDNA genes.

FIG. 1. Schematic of an acrylic column reactor used for enrichment of oil consuming strains.

Figure 2A:
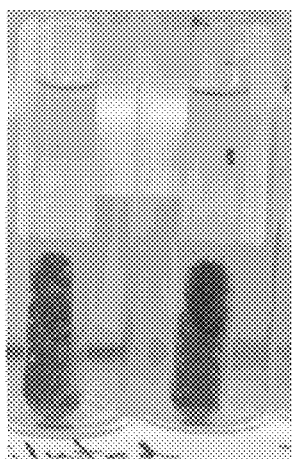
Figure 2B:
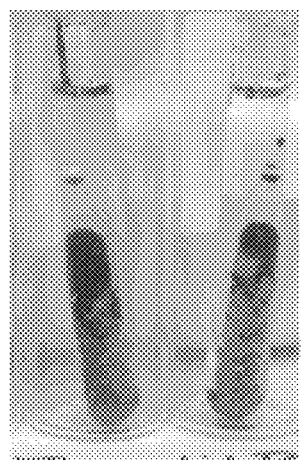
Figure 2C:
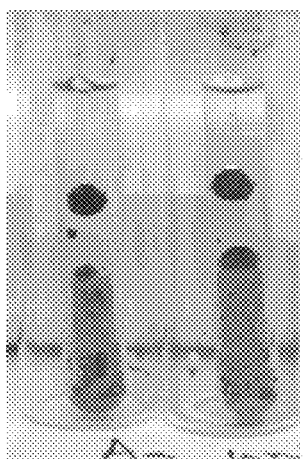

FIG. 2. A micro sand column oil release assay showing release of oil droplets. A. Control (no release); B. Droplets on surface (partial release); C. Oil in pipet neck (full release).

Figure 3:
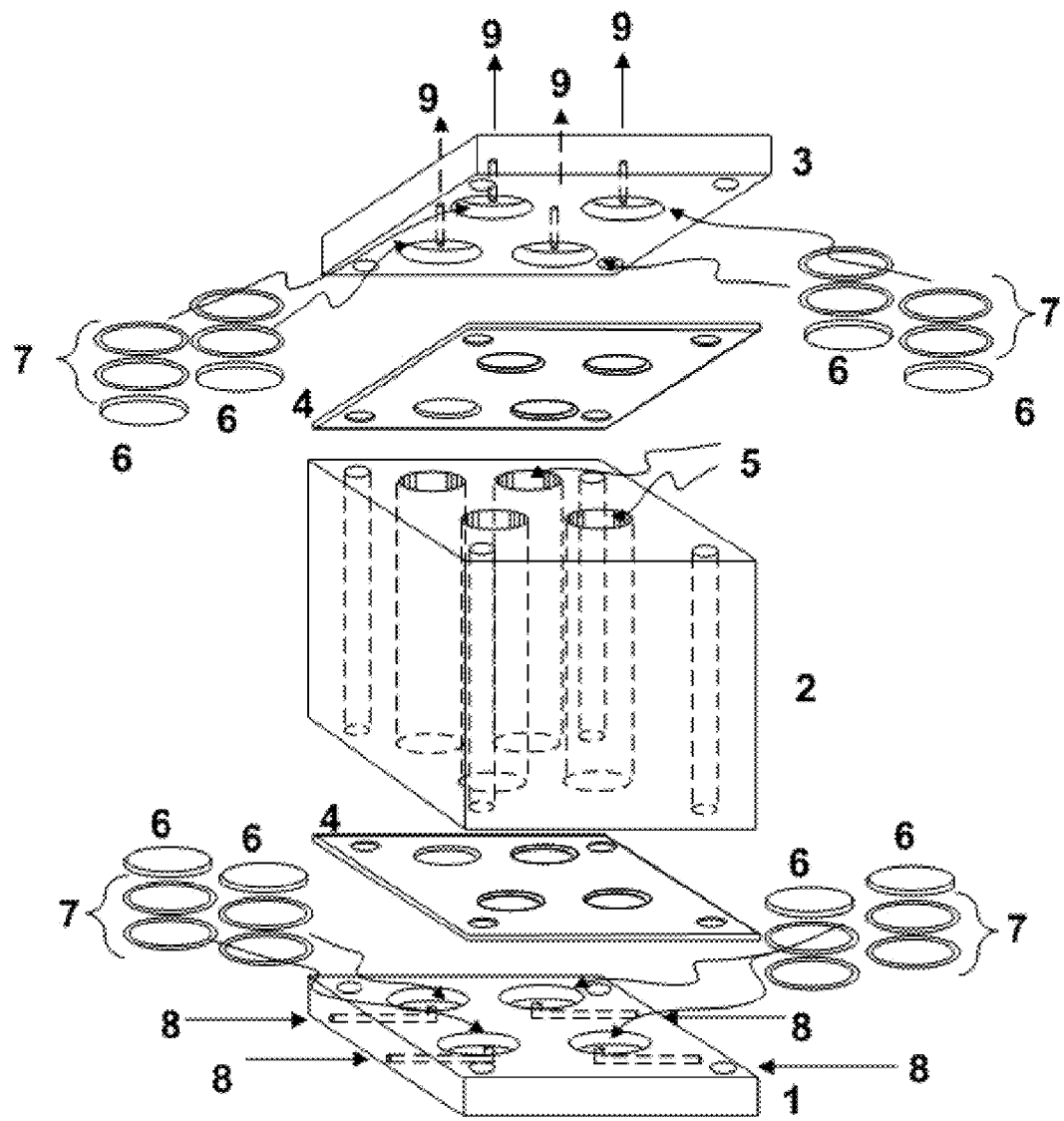

FIG. 3. Construction of mini sandpack column for oil release.

Figure 4:
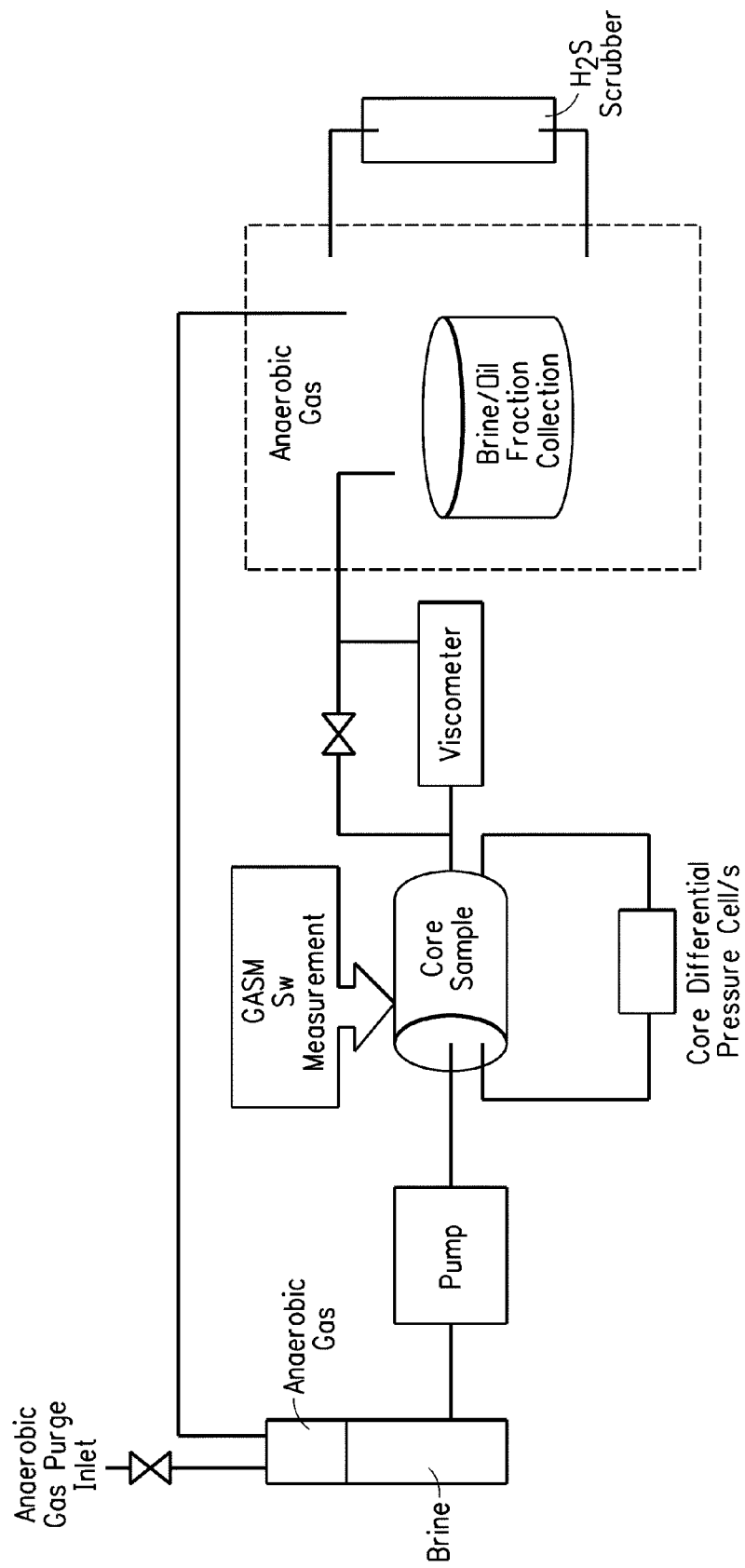

FIG. 4. Diagram of compressed sandpack oil release apparatus.

Figure 5:
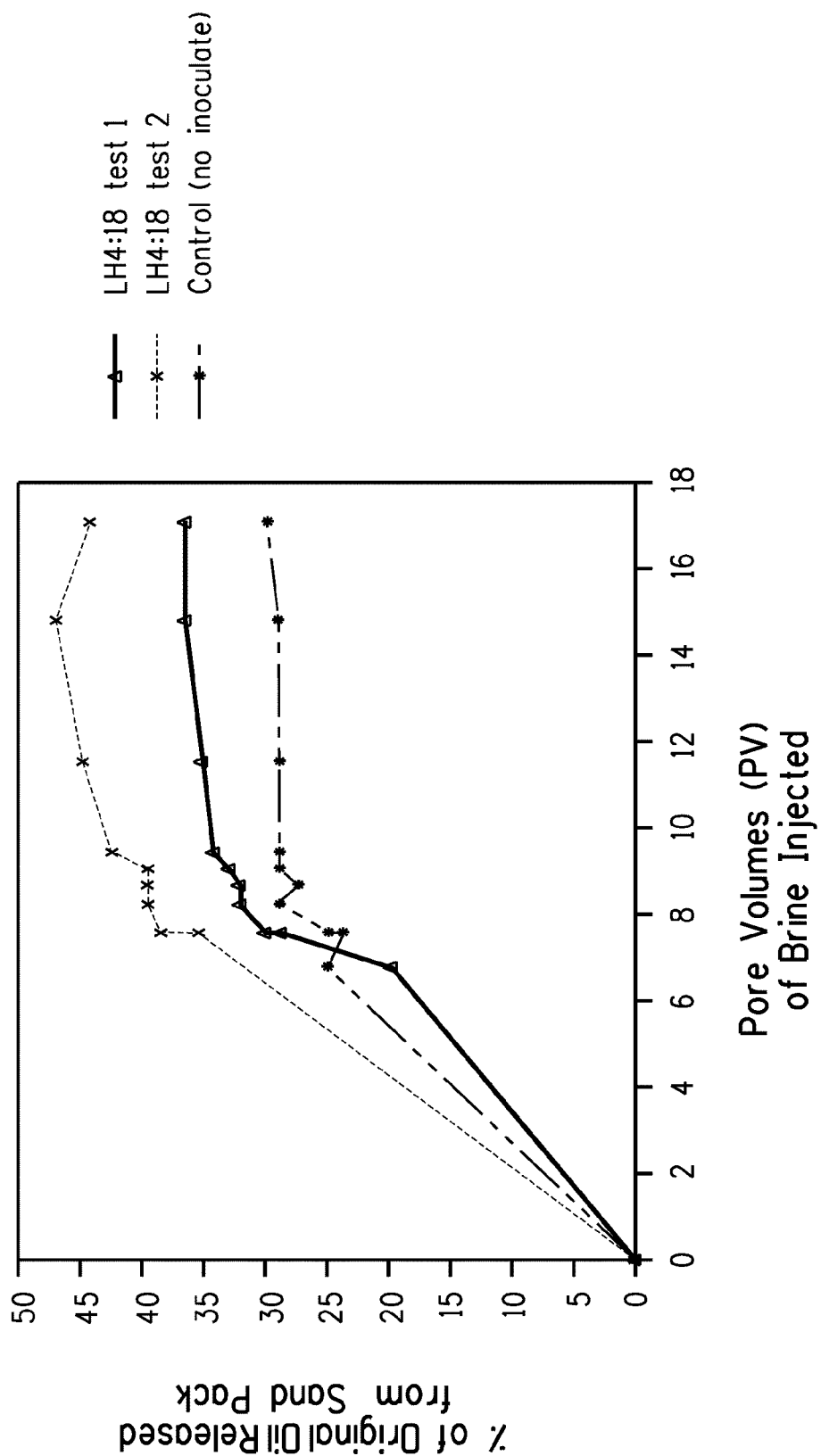

FIG. 5. Graph of oil release over time in a mini sandpack test inoculated with bacterial isolate *Shewanella putrefaciens* LH4:18.

Figure 6:
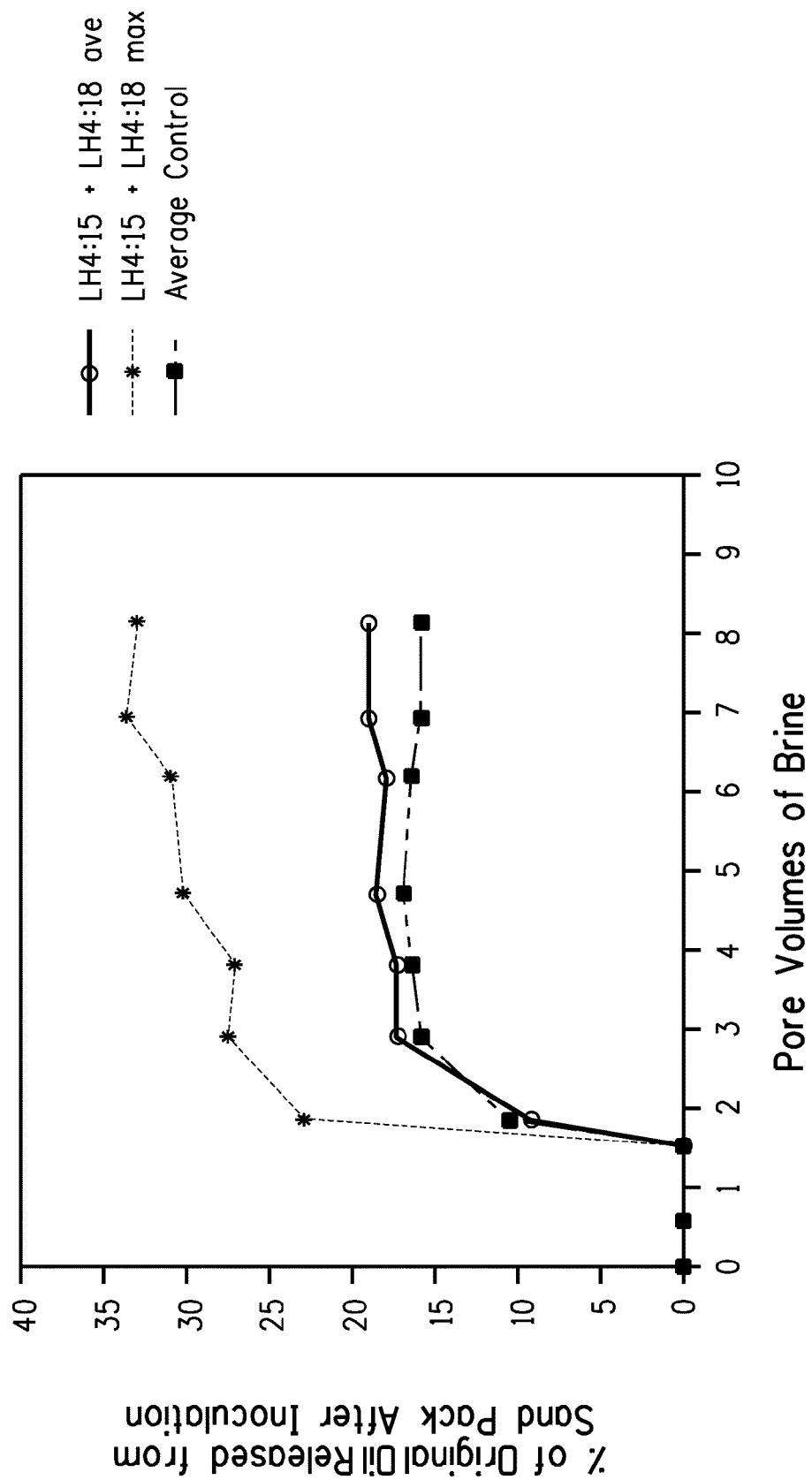

FIG. 6. Graph of oil release over time in a mini sandpack test inoculated with bacterial isolate *Shewanella putrefaciens* LH4:18 mixed with bacterial isolate *Pseudomonas stutzeri* LH4:15.

Figure 7:
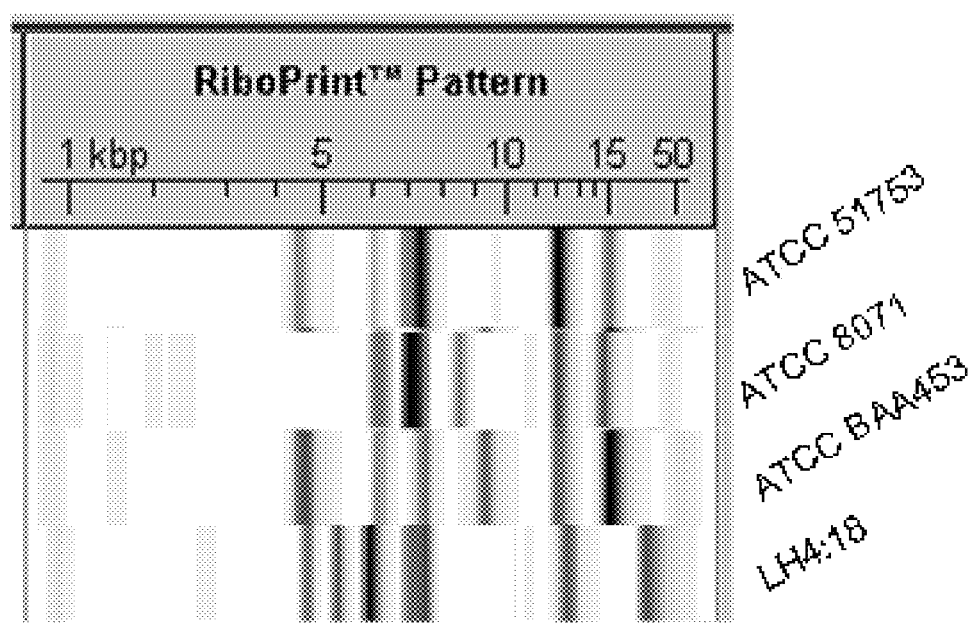

FIG. 7. Results of Riboprinter analysis of *Shewanella* strains.

Applicants made the following biological deposits under the terms of the Budapest Treaty on the International Recognition of the Deposit of Microorganisms for the Purposes of Patent Procedure:

TABLE 1

INFORMATION ON DEPOSITED STRAINS

| Depositor Identification Reference | International Depository Designation | Date of Deposit |
|---|---|---|
| *Shewenella putrefaciens* LH4:18 | ATCC No. PTA-8822 | Dec. 4, 2007 |
| *Pseudomonas stutzeri* LH4:15 | ATCC No. PTA-8823 | Dec. 4, 2007 |

DETAILED DESCRIPTION OF THE INVENTION

The invention relates to the identification of a previously unknown microorganism from production water samples obtained from an oil reservoir. A screening protocol was developed to identify microbes capable of growth under denitrifying conditions using oil or oil components as the sole source of carbon. These microbes could be grown in situ in an oil reservoir for enhancement of oil recovery The following definitions are provided for the special terms and abbreviations used in this application:

The abbreviation "dNTPs" refers to Deoxyribonucleotide triphosphates.

The abbreviation "ATCC" refers to American Type Culture Collection International Depository, Manassas, Va., USA. "ATCC No." refers to the accession number to cultures on deposit with ATCC.

The abbreviation "ASTM" refers to the American Society for Testing and Materials.

The term "environmental sample" means any sample exposed to hydrocarbons, including a mixture of water and oil. As used herein environmental samples include water and oil samples that comprise indigenous microorganisms useful for phylogenetic mapping of genera present in a given sampling area.

The terms "oil well" and "oil reservoir" may be used herein interchangeably and refer to a subterranean or sea-bed formation from which oil may be recovered.

The term "improving oil recovery" refers to the use of hydrocarbon-utilizing microorganisms, which are endemic in petroleum reservoirs, where they occur naturally using hydrocarbons as a food source. As a result of this process, through excretion of bio-products such as alcohols, gases, acids, surfactants and polymers, hydrocarbon-utilizing microorganisms can change the physico-chemical properties of the crude oil. Changed physico-chemical properties are, e.g., those described under the term "modifying the environment of oil well", infra.

The term "growing on oil" means the microbial species are capable of metabolizing hydrocarbons or other organic components of crude petroleum as a nutrient to support growth.

The term "electron acceptor" refers to a chemical entity that accepts electrons transferred to it from another compound. It is an oxidizing agent that, by virtue of its accepting electrons, is itself reduced in the process.

The terms "denitrifying" and "denitrification" mean reducing nitrate for use in respiratory energy generation.

The term "sweep efficiency" means the ability of injected water to 'push' oil through a geological formation toward a producer well. One problem that can be encountered with waterflooding operations is the relatively poor sweep efficiency of the water, i.e., the water can channel through certain portions of the reservoir as it travels from the injection well(s) to the production well(s), thereby bypassing other portions of the reservoir. Poor sweep efficiency may be due, for example, to differences in the mobility of the water versus that of the oil, and permeability variations within the reservoir which encourage flow through some portions of the reservoir and not others.

The term "pure culture" means a culture derived from a single cell isolate of a microbial species. The pure cultures specifically referred to herein include those that are publicly available in a depository. Additional pure cultures are identifiable by the methods described herein.

The term "biofilm" means a film or "biomass layer" of microorganisms. Biofilms are often embedded in extracellular polymers, which adhere to surfaces submerged in, or subjected to, aquatic environments.

The term "simple nitrates" and "simple nitrites" refer to nitrite ($NO_2$) and nitrate ($NO_3$).

"Injection Water" means water used to inject into oil reservoirs for secondary oil recovery.

The term "modifying the environment of oil well" includes one or more of 1) altering the permeability distribution of the subterranean formation (sweep efficiency), (2) producing biosurfactants which decrease surface and interfacial tensions, (3) mediating changes in wettability, (4) producing polymers that improve the oil/water mobility ratio; (5) generating gases (predominantly $CO_2$) that increase formation pressure; and (6) reducing oil viscosity.

The abbreviation "NCBI" refers to the National Center for Biotechnology Information.

The term "phylogenetic typing", "phylogenetic mapping", or "phylogenetic classification" may be used interchangeably herein and refer to a form of classification in which microorganisms are grouped according to their ancestral lineage. The methods herein are specifically directed to phylogenetic typing on environmental samples based on 16S Ribosomal DNA (rDNA) sequencing. In this context, a full 1400 base pair (bp) length of the 16S rDNA gene sequence is generated using primers identified herein and compared by sequence homology to a database of known rDNA sequences of known microorganisms. This comparison is then used for identification of pure cultures for use in enhanced oil recovery.

The term "ribotyping" means fingerprinting of genomic DNA restriction fragments that contain all or part of the genes coding for the 16S and 23S rRNA.

The term "microbial species" means distinct microorganisms identified based on their physiology, morphology and phylogenetic characteristics using 16S rDNA sequences.

The abbreviation "rDNA" refers to Ribosomal Deoxyribonucleic Acid.

The term "rDNA typing" means the process of utilizing the sequence of the gene coding for 16S rDNA to obtain the "closest relative" microbial species by homology to rDNA sequences maintained in several international databases.

The term "sequence analysis software" refers to any computer algorithm or software program that is useful for the analysis of nucleotide or amino acid sequences. "Sequence analysis software" may be commercially available or independently developed. Typical sequence analysis software includes, but is not limited to: the GCG suite of programs (Wisconsin Package Version 9.0, Genetics Computer Group (GCG), Madison, Wis.), BLASTP, BLASTN, BLASTX (Altschul et al., *J. Mol. Biol.* 215, 403-410, 1990), DNASTAR (DNASTAR, Inc., Madison, Wis.), and the FASTA program incorporating the Smith-Waterman algorithm (Pearson, W. R., *Comput. Methods Genome Res.*, Proc. Int. Symp, Meeting Date 1992, 111-120, Eds: Suhai, Sandor, Plenum Publishing, New York, N.Y., 1994). Within the context of this application, it will be understood that, where sequence analysis software is used for analysis, the results of the analysis will be based on the "default values" of the program referenced, unless otherwise specified. As used herein "default values" will mean any set of values or parameters which originally load with the software when first initialized.

Additional abbreviations used in this application are as follows: "hr" means hour(s), "min" means minute(s), "day" means day(s), "mL" means milliliters, "mg/ml" means milligram per milliliter, "L" means liters, "µL" means microliters, "mM" means millimolar, "µM" means micromolar, "nM" means nano molar, "µg/l" means microgram per liter, "µmol" means picomol(s), "° C." means degrees Centigrade, "° F." means degrees Fahrenheit, "bp" means base pair, "bps" means base pairs, "mm" means millimeter, "ppm" means part permillion, "g/l" means gram per liter, "ml/min" means milliliter per minute, "ml/hr" means milliliter per hour, "cfu/ml" means colony forming units per milliliter, "g" means gram, "mg/L" means milligram per liter, "Kev" means kilo or thousands of electron volts, "psig" means per square inch per gram, "LB" means Luria broth, "rpm" means revolution per minute.

Growth of Microorganisms

Techniques for growth and maintenance of anaerobic cultures are described in "Isolation of Biotechnological Organisms from Nature", (Labeda, D. P. ed. 117-140, McGraw-Hill Publishers, 1990). Anaerobic growth is measured by nitrate depletion from the growth medium over time. Nitrate is utilized as the primary electron acceptor under the growth conditions used herein. The reduction of nitrate to nitrogen has been previously described (Moreno-Vivian, C., et al., J. Bacteriol., 181, 6573-6584, 1999). In some cases nitrate reduction processes lead to nitrite accumulation which is subsequently further reduced to nitrogen. Accumulation of nitrite is therefore also considered evidence for active growth and metabolism by microorganisms.

Ion Chromatography

To quantitate nitrate and nitrite ions in aqueous media, Applicants used an ICS2000 chromatography unit (Dionex, Banockburn, Ill.) equipped with an AS15 anion exchange column and a gradient of 2 to 50 mM potassium hydroxide. Standard curves using known amounts of sodium nitrite or sodium nitrate solutions were generated and used for calibrating nitrate and nitrite concentrations.

Screening to Discover Environmental Isolates Capable of Growth on Oil Components A screening protocol to discover novel pure cultures capable of growth on and/or modification of petroleum components was implemented as follows:

Samples from Oil Reservoir Production Water.

Water samples were obtained from production and injection well heads as mixed oil/water liquids in glass 1.0 L brown bottles, filled to the top, capped and sealed with tape to prevent gas leakage. Gas from inherent anaerobic processes sufficed to maintain anaerobic conditions during shipment. The bottles were shipped in large plastic coolers filled with ice blocks to the testing facilities within 48 hr of sampling.

Column Enrichment

Column reactors were used to develop enrichment cultures from industrial and environmental samples to select for a diversity of organisms that would grow on oil for use in MEOR. The use of column reactors has previously been reported (Fallon, R. D., et al., *Appl. Environ. Microbiol.*, 57, 1656-1662, 1991). An acrylic column reactor (3 inch diameter by 24 inch length, shown in FIG. 1) was used. The column had 9 side ports (FIG. 1 (E)), and each side port had a ⅛ inch National Pipe Thread (NPT) female threads tapped into it. A male ⅛ inch pipe to ⅛ female swagelock tube fitting adapter (Swagelok Company, Solon, Ohio) was mounted into this threaded hole. Into the ⅛ inch tube end of this fitting was mounted a septum so that a syringe needle could be used to later sample the column. This mounting was made air tight as evidenced by the fact that no water leaked when the column was filled with water. The column was mounted vertically as indicated in FIG. 1. Each of the fittings was located along the side of the column at intervals of 2 inches height. At both ends of this column, common 80 mesh screen and ordinary glass wool were mounted and later used (as described below) to contain ocean sand in the column. At the top and bottom of the column were empty sections (FIGS. 1, (C) and (D)). Each of these empty sections was 3 inches long and 3 inches in diameter. Holes were machined into each of these empty sections and ⅛ inch NPT female threads were cut and a male ⅛ inch pipe to ⅛ female swagelock tube fitting adapter (Swagelok Company) was mounted into this threaded hole. The port at the bottom empty section was connected to a syringe pump via ⅛ inch diameter stainless steel tubing (FIG. 1 (A)). The port from the top empty section overflowed (FIG. 1 (F)) and was connected to a collection container that was blanketed with nitrogen gas. The head space of this top section was vented to a nitrogen purged bubbler (FIGS. 1, (G) and (H)). The top empty section of the column was temporarily removed and Ocean Sand (SX0076-1, LOT#46257714, EMD Chemicals Inc, Gibbstown, N.J.) was poured into the column so that it filled about 50% of the column. The sand was held in place by the glass wool and 80 mesh screen described above.

Crude oil from the Alaskan North Slope was used in Examples 2-5. This same crude oil batch was distilled following ASTM method 2892 (Standard Test Method for Distillation of Crude Petroleum (15-Theoretical Plate Column), Designation: D 2892-05, at ASTM International Standards Worldwide at http://www.Astm.org/D2892.htm, pp. 1-32). A portion of the still bottoms collected at a temperature of >610° F. (>321.1° C.) was used in a subsequent distillation following the ASTM method 5236 (Standard Test Method for distillation of Heavy Hydrocarbon Mixtures, Designation D5236-03 at http://www.Astm.orq/D5236.htm, pp. 1-18). About 400 g of the still bottoms collected at >1005° F. (>540.6° C.) from this distillation was dissolved in 100 g of toluene to make a flowable solution. This solution was poured onto the sand that was loaded in the bottom half of the column. Additional fresh ocean sand was then added to fill the column, and the >610° F. (>321.1° C.) still bottom collected from the ASTM 2892 distillation was poured onto this portion of fresh sand. The top empty section was replaced. The ⅛ tubing attached to the bottom section (FIG. 1 (A)) was disconnected from the syringe pump and connected instead to a source of low pressure (5 psig) nitrogen. Nitrogen was blown in through this ⅛ inch tubing attached to the bottom of the column for 4 days to evaporate any toluene. At the end of this four day period, the ⅛ inch tubing (FIG. 1 (A)) was disconnected from the nitrogen source and the syringe pump was reattached. Using the syringe pump and ⅛ inch tubing attached to the bottom of the column, the column was fed and saturated with a complete medium containing nitrate with composition essentially as in Table 2 except the base salts were 60 mg/L $CaCl_2.2H_2O$; 400 mg/L $MgSO_4.7H_2O$; 400 mg/L KCl; 40 mg/L $NaH_2PO_4$; 500 mg/L $NH_4Cl$; 2g/L $NaHCO_3$; 400 mg/L $NaNO_3$; and 3 g/L NaCl. The column was then inoculated with water collected from the oil well production and water injection wells from Alaska North Slope oil fields. After inoculation, the column was allowed to sit for a week. After this period, the complete medium with nitrate was continuously fed at a rate of 1 ml/hr. Samples were periodically taken using syringes piercing through the septum sealed sampling ports (FIG. 1 (E)) described above, along the side of the column. In this manner, microbes were harvested for use in subsequent enrichment cultures. The microorganism mixes enriched in these reactors were used to isolate strains that grow either on oil or in the presence of oil. Culture LH4:18 was derived by taking samples from the lower ports on this column at 6 months post inoculation, diluting ×1,000 and streaking on standard Luria Broth (Teknova, Hollister, Calif.) agar plates. Isolated colonies were selected for subsequent screening by 16S rDNA typing and oil release tests.

Direct Colony rDNA Sequence Analysis

Genomic DNA from bacterial colonies was isolated by diluting bacterial colonies in 50 µL of water. Diluted colony DNAs were amplified with Phi 29 DNA polymerase prior to sequencing (GenomiPHI Amplification Kit GE Life Sciences, New Brunswick, N.J.). An aliquot (1.0 µL) of the diluted colony was added to 9.0 µL of the Lysis Reagent (from the GenomiPHI Amplification Kit) and heated to 95° C. for 3.0 min followed by immediate cooling to 4° C. 9.0 µL of Enzyme Buffer and 1.0 µL of Phi 29 enzyme were added to each lysed sample followed by incubation at 30° C. for 18 hr. The polymerase was inactivated by heating to 65° C. for 10 min followed by cooling to 4° C.

DNA sequencing reactions were set up as follows: 8.0 µL of GenomiPHI amplified sample were added to 8.0 µL of BigDye v3.1 Sequencing reagent (Applied Biosystems, Foster City, Calif.) followed by 3.0 µL of 10 µM primers SEQ ID NOs: 1 and 2 (prepared by Sigma Genosys, Woodlands, Tex.), 4.0 µL of 5×BigDye Dilution buffer (Applied Biosystems) and 17 µL Molecular Biology Grade water (Mediatech, Inc., Herndon, Va.).

Sequencing reactions were heated for 3.0 min at 96° C. followed by 200 thermocycles of (95° C. for 30 sec; 55° C. for 20 sec; 60° C. for 2 min) and stored at 4° C. Unincorporated dNTPs were removed using Edge Biosystems (Gaithersburg, Md.) clean-up plates. Amplified reactions were pipetted into one well of a pre-spun 96 well clean up plate. The plate was centrifuged for 5.0 min at 5,000×g in a Sorvall RT-7 (Sorvall, Newtown, Conn.) at 25° C. The cleaned up reactions were placed directly onto an Applied Biosystems 3730 DNA sequencer and sequenced with automatic basecalling.

Each of the assembled rDNA sequences was compared to the NCBI rDNA database (~260,000 rDNA sequences) using the BLAST algorithm (Altschul et al. (supra)). The primary hit was used as an identifier of the most closely related known species identification. The initial screen using the rDNA colony direct sequencing reduced the number of colonies to be carried through further screening by 20 fold. The unique isolate set was then used to screen for growth on oil as a sole carbon source under denitrifying conditions.

Micro Sand Column Oil Release Test

Isolated bacterial strains were examined using a micro sand column assay to visualize oil release. A micro sand column consisted of an inverted glass Pasteur pipet containing sea sand (EMD chemicals, La Jolla, Calif.) which had been coated with crude oil and allowed to age for at least one week. Specifically, 280 mL of sterile sand and 84 mL of sterilized oil (same oil used in Examples 2 though 5) were combined in an anaerobic environment. The mixture was stirred for 5 min twice each day and allowed to age for six days under nitrogen. The barrels of glass Pasteur pipets were cut to half height and autoclaved. The cut end of the pipet was plunged into the sand/oil mix and the core filled to about 1.0 inch. The cut end of the pipet containing the oil/sand mixture was then placed into a glass test tube containing microbial cultures. The apparatus was sealed inside glass vials in an anaerobic environment and the oil release from the sand observed in the tapered end of each pipet (FIG. 2). Oil released from the sand collects in the narrow neck of the Pasteur pipets or as droplets on the surface of the sand layer. Cultures which enhanced release of oil over background (sterile medium) were presumed to have altered the interaction of the oil with the sand surface and could potentially act to enhance oil recovery in a petroleum reservoir.

Mini Sandpack Experiments to Observe Oil Release

Mini sandpack experiments were done in parallel in a multi-well apparatus similar to that described by J. D. Levi, et al. (*Intl. BioRes. J.*, 1, 336, 1985). A multiwell apparatus (FIG. 3) was constructed as follows: A five inch thick aluminum block (FIG. 3, (2)) was machined with a series of 5 inch long, ⅞ inch diameter holes (FIG. 3, (5)). In FIG. 3, four of these holes are shown although in subsequent tests a block with more holes was used. A 1 inch thick aluminum plate (FIG. 3, (1)) was machined with ¼ inch deep by 1 inch diameter wells. These wells were concentric with the holes machined into the 5 inch thick block. Small, ⅛ inch diameter holes (FIG. 3, (8)) were machined under the ¼ inch by 1 inch diameter wells and out to a side of the 1 inch thick block (FIG. 3, (1)). ⅛ inch pipe threads were machined into the outside face of the block and swagelock fittings (Swagelok Company) were mounted onto the side of the block to allow ⅛ inch tubing connections to these wells. These connectors were connected via ⅛ inch tubing to a series of syringe pumps—one pump being connected to each hole. A second 1 inch aluminum block (FIG. 3, (3)) was machined in the same manner. Two ⅛ inch thick neoprene rubber mats (FIG. 3, (4)) were cut the same size as the 1 inch thick blocks and ⅞ inch diameter holes with the same hole pattern as the blocks were cut into the rubber mats. Into each 1 inch thick plate (FIG. 3, (1) and (3)) was mounted a 1 inch diameter fritted glass filter (FIG. 3, (6)) (Chemglass Scientific Apparatus, Vineland, N.J.). This glass frit was sealed to each plate using a series of "0" rings (FIG. 3, (7)) (Parker Hannifin Corporation, O-Ring Division, Lexington, Ky.). The one inch thick plate with the syringe pump feed lines (FIG. 3, (1)) was covered with the neoprene gasket (FIG. 3, (4)), and the 5 inch thick block (FIG. 3, (2)) was bolted to the gasket (FIG. 3, (4)) in such a fashion that the wells in the bottom plate were in communication with the wells in the 5 inch thick block. All plates and equipment were sterilized by autoclaving prior to completing the assembly.

Six wells were then packed with an aged oil/sand mixed as follows: 403.2 mL of sterilized ocean sand (SX0076-1, LOT# 46257714, EMD Chemicals Inc., Gibbstown, N.J.) was combined with 151.2 mL of the same sterile crude oil from the Alaskan North Slope. This is the same oil used in Examples 2 through 6. The oil and sand were combined under a nitrogen atmosphere and thoroughly mixed. This oil soaked sand mixture was aged for six days with additional mixing being done once or twice per day. This mixture was then packed into the six wells (FIG. 3, (5)) of the 5 inch block (FIG. 3, (2)). The second neoprene gasket (FIG. 3, (4)) was placed on the top of the 5 inch thick block and the second 1 inch thick plate (FIG. 3, (3)) with the glass frits (FIG. 3, (6)) and O ring seals (FIG. 3, (7)) as described for the other plate were bolted to the 5 inch block in such a way that the wells in the 1 inch plate were in communication with the wells that had the oil soaked sand packed into them. From the top of this second one inch plate, small holes were bored through the top and connected to ⅛ inch diameter tubing (FIG. 3, (9)). This tubing was run directly into a simple oil-water separator. This separator is very similar to that described in described by J. D. Levi, et al., supra. It consisted of a ⅛ inch diameter tube pushed through a bored out ⅛ inch by ½ inch tube reducer (Swagelok Company). This ⅛ inch diameter tube was placed concentric in a ½ inch Teflon tube that formed a stand leg for the oil/water separator. At the bottom of the Teflon tube, but below the top end of the ⅛ inch tube, was a "tee". The produced fluid from the sandpack was allowed to flow up through the ⅛ inch dip tube past the tee. The oil would float to the top of the stand leg above the tee. Water in the stand leg that was displaced went out the side port of the tee below the oil and up through a ⅛ inch flexible tube. This tube was configured so that it ran up to a height that was just below the top of the oil stand leg. This tube then was directed to a separate water collection jug. Thus the total height of liquid in the ½ inch oil stand leg was fixed, and oil that was released from the sandpack could be measured as the height of oil in the ½ inch diameter Teflon stand leg (vertical tube that acted as an oil collector).

Sandpack Oil Release Analysis

Selected microbes were used in a hydraulically confined sandpack test. Two sandpack tests were done to illustrate the utility and sensitivity of this invention. Example 5 illustrates how the sandpack was calibrated on crude oil and a water solution that was created to mimic the composition of the injection brine used in water flooding of a target oil reservoir. Example 6 illustrates use of the sandpack using the same fluids but with the addition of microbes after an initial flooding period. FIG. 4 is the diagram of the sandpack apparatus.

Sandpack or core flood equipment are well known in the petroleum exploration literature (Petroleum Reservoir Rock and Fluid Properties, Abhijit Y. Dandehar, CRC Press, 2006). In addition, a similar core flood/sandpack apparatus and techniques used to operate it are described by Berry et al. (SPE paper number 200056, "In-Situ Saturation Measurements Improve Analysis and Interpretation of Laboratory Miscible and Immiscible Displacement Processes", SPE Reservoir Engineering, November 1991, p. 429). The use of similar apparatus and techniques for testing microbial treatments in a sandpack is described by Saikrishna M. et al. (SPE paper number 89473, 2004, "Development of Bio-surfactant Based Microbial Enhanced Oil Recovery Procedure").

Automated Ribotyping

Automated ribotyping was used for conclusive identification of selected strains with similar 16S rDNA sequence phylogenetic characteristics (Bruce, J. L., 1996. *Food Technology*, 50, 77-81, 1996 and Sethi, M. R., *Am. Lab.* 5, 31-35, 1997). Ribotyping was performed as recommended by the manufacturer (DuPont Qualicon Inc., Wilmington, Del.). For these analyses, one fresh colony was picked, resuspended in the sample buffer and added to the processing module for the heat treatment step at 80° C. for 10 min to inhibit endogenous DNA-degrading enzymes. The temperature was then reduced, and two lytic enzymes (lysostaphin and N-acetyl-muramidase) (provided by the manufacturer) were added to the sample. The sample carrier was then loaded onto the Riboprinter system with the other commercial reagents. Restriction enzyme digestion using EcoRI enzyme, gel electrophoresis and blotting steps were completely automated. Briefly, bacterial DNA was digested with the EcoRI restriction enzyme and loaded onto an agarose gel: restriction fragments were separated by electrophoresis and simultaneously transferred to a nylon membrane. After a denaturation step, the nucleic acids were hybridized with a sulfonated DNA probe harboring the genes for the small and large rRNA subunits of *E. coli*. The hybridized probe was detected by capturing light emission from a chemiluminescent substrate with a charge-coupled device camera. The output consisted of a densitometric scan depicting the distribution of the EcoRI restriction fragments containing the 16S or 23S rDNA sequences and their molecular weights.

Bioremediation and Oil Pipeline Maintenance

The ability of *Shewanella putrefaciens* LH4:18 to metabolize hydrocarbons makes this strain useful in the bioremediation of areas contaminated with hydrocarbons. Thus, also provided herein are methods for decontaminating or remediating contaminated areas by applying to the area(s) bacterial isolate *Shewanella putrefaciens* LH4:18, which is then allowed to metabolize or mobilize the contaminants in situ. Bioremediation takes place when *Shewanella putrefaciens* LH4:18 cells are exposed to hydrocarbons and convert them into products such as, e.g., carbon dioxide, water, and oxygen or when the growth of the LH4:18 cells allows release of high molecular weight hydrocarbons to the surface for subsequent removal by physical clean up processes. In some embodiments, *Shewanella putrefaciens* LH4:18 can be incubated in the environment to be bioremediated without any added cosubstrate, or other carbon or energy source. The bioremediation process can be monitored by periodically taking samples of the contaminated environment, extracting the hydrocarbons, and analyzing the extract using methods known to one skilled in the art.

Contaminated substrates that may be treated with *Shewanella putrefaciens* LH4:18 include, but are not limited to, harbor dredge spoils, sediments, wastewater, sea water, soil, sand, sludge, air, and refinery wastes. In another embodiment, the contaminated substrate can be an oil pipeline. Hydrocarbon incrustation and sludge buildup are significant causes of decreased pipeline performance and can eventually lead to failure of the pipeline. Because of the ability of *Shewanella putrefaciens* LH4:18 to release hydrocarbons, application of LH4:18 to an oil pipeline containing incrusted hydrocarbons or hydrocarbon-containing sludge can be useful in the removal of the unwanted hydrocarbons from the pipeline.

In some embodiments, other agents effective in the bioremediation of hydrocarbons can be added to a *Shewanella putrefaciens* LH4:18 bioremediation composition. These other agents may include a microorganism or more than one microorganism, such as a bacterium, a yeast, or a fungus. The agents may also include a chemical compound that is not lethal to *Shewanella putrefaciens* LH4:18, but is effective at degrading or partially degrading hydrocarbons and/or other contaminants or stimulating growth of *Shewanella* LH4:18 to effect oil release. In some embodiments, the additional agent is *Pseudomonas stutzeri* strain LH4:15, which is described in the commonly owned, co-filed, and co-pending application U.S. Ser. No. 12/105,769.

Microorganisms may be delivered to the contaminated substrate by any one of the many well known methods including those described in, e.g., Newcombe, D. A., and D. E. Crowley (Appl. Microbiol. Biotechnol. 51:877-82, 1999); Barbeau, C. et al. (Appl. Microbiol. Biotechnol. 48:745-52, 1997); U.S. Pat. Nos. 6,573,087, 6,087,155, and 5,877,014.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Anaerobic Growth of Bacterial Isolates on Oil as the Sole Carbon Source

To study growth of isolated colonies from long term column cultures on crude oil as a sole carbon source under anaerobic conditions, purified isolates were inoculated into 20 mL serum vials containing 10 mL minimal salts medium (Table 2), 1.6 g/l sodium nitrate and 5.0 mL of autoclaved crude oil. The medium was deoxygenated by sparging the filled vials with a mixture of nitrogen and carbon dioxide followed by autoclaving. All manipulations of bacteria were done in an anaerobic chamber (Coy Laboratories Products, Inc., Grass Lake, Mich.). The cultures were incubated at ambient temperatures with moderate shaking (100 rpm) for several weeks to several months and monitored for nitrate, nitrite, visible turbidity and visible oil modifications. When the nitrate was depleted in any culture, sodium nitrate at 50 g/l was added to bring its concentration in the medium up to 0.4 g/l sodium nitrate.

TABLE 2

MINIMAL SALTS MEDIUM

| Growth component | Final concentration | Chemical source |
|---|---|---|
| Nitrogen | 18.7 µM | $NH_4Cl$ |
| Phosphorus | 3.7 µM | $KH_2PO_4$ |
| Magnesium | 984 µM | $MgCl_2 \cdot 6H_2O$ |
| Calcium | 680 µM | $CaCL_2 \cdot 2H_2O$ |
| Sodium chloride | 172 mM | NaCl |
| Trace metals | 670 µM | nitrilotriacetic acid |
|  | 15.1 µM | $FeCl_2 \cdot 4H_2O$ |
|  | 1.2 µM | $CuCl_2 \cdot 2H_2O$ |
|  | 5.1 µM | $MnCL_2 \cdot 4H_2O$ |
|  | 12.6 µM | $CoCl_2 \cdot 6H_2O$ |
|  | 7.3 µM | $ZnCl_2$ |
|  | 1.6 µM | $H_3BO_3$ |
|  | 0.4 µM | $Na_2MoO_4 \cdot 2H_2O$ |
|  | 7.6 µM | $NiCl_2 \cdot 6H_2O$ |
| pH buffer (7.5 final) | 10 mM | Hepes |
| Selenium-tungstate | 22.8 nM | $Na_2SeO_3 \cdot 5H_2O$ |
|  | 24.3 nM | $Na_2WO_4 \cdot 2H_2O$ |
| Bicarbonate | 23.8 nM | $NaHCO_3$ |
| vitamins | 100 µg/l | vitamin B12 |
|  | 80 µg/l | p-aminobenzoic acid |
|  | 20 µg/l | nicotinic acid |
|  | 100 µg/l | calcium pantothenate |
|  | 300 µg/l | pyridoxine hydrochloride |
|  | 200 µg/l | thiamine-HCl·$2H_2O$ |
|  | 50 µg/l | alpha-lipoic acid |
| Electron acceptor | 0.4 g/l | $NaNO_3$ |

The pH of the medium was adjusted to 7.5.

Table 3 shows the results of these growth studies. Pure cultures which showed growth via nitrate reduction and turbidity increase under denitrifying conditions were chosen as "capable of growth on oil under denitrifying conditions" and were subjected to several tests for oil release phenomenona as described below. One strain, designated LH4:18, was identified by 16S rDNA typing as homologous to *Shewanella putrefaciens* (strain CN32). A single colony of this isolate was inoculated onto the medium described above containing 200 ppm of nitrate. Strain LH4:18 grew on oil as the sole source of carbon and depleted 40 ppm of nitrate in 60 days.

TABLE 3

NITRATE REDUCTION AS A MEASURE OF ANAEROBIC GROWTH WITH OIL AS THE SOLE CARBON SOURCE

| Bacterial isolate | % nitrate reduction | time to reduction (months) |
|---|---|---|
| *Marinobacterium* sp. LH4:4 | 0 |  |
| Unknown sp. LH4:7 | 0 |  |
| *Pseudomonas stutzeri* LH4:15 | 52 | 2 |
| *Shewanella putrefaciens* LH4:18 | 20 | 2 |
| *Thauera* sp. LH4:37 | 0 |  |
| Unknown sp. LH4:38 | 0 |  |
| *Pseudomonas stutzeri* MO LCED3 | 12 | 2 |

Example 2

Screening of Bacterial Isolates for Enhanced Oil Release

In this Example, inoculum was grown to turbidity using the minimal salts medium shown in Table 2 with 0.4% succinate as carbon source. The concentration of each species, listed in Table 4 below, was normalized to $OD_{600}$ of 1.0 or diluted 1:10 for a final $OD_{600}$ of 0.1. All operations for preparation of the micro sand columns, inoculation and growth were done using sterile techniques in an anaerobic glove bag. Inocula (4 mL) from either the $OD_{600}$ of 1.0 or $OD_{600}$ Of 0.1 were added to small glass tubes and the micro sand columns immersed in the medium/cell mixtures with the narrow neck of the Pasteur pipets pointing up. The outer vials were sealed in the anaerobic chamber and allowed to incubate at ambient temperatures for 24 hr. Table 4 shows the strains tested and the observations of oil release after 24 hr.

TABLE 4

RELEASE OF OIL FROM MICROSAND COLUMNS BY ISOLATED BACTERIAL STRAINS

| Bacterial isolate | inoculum $OD_{600}$ = 1 | inoculum $OD_{600}$ = 0.1 |
|---|---|---|
| Unknown sp. LH4:3 | n.d. | n.d. |
| Unknown sp. LH4:4 | no release | no release |
| Unknown sp. LH4:7 | no release | n.d. |
| *Pseudomonas stutzeri* LH4:15 | no release | oil release |
| *Shewanella putrefaciens* LH4:18 | oil release | no release |
| *Thauera* sp. LH4:37 | oil release | oil release |
| Unknown sp. LH4:38 | no release | no release |
| *Pseudomonas stutzeri* MO LCED3 | no release | oil release |

Cultures were 16S rDNA typed to confirm pure isolate conservation at several points in these studies. Pure isolates which had interesting attributes in these tests were further screened for oil release enhancement in a larger scale version of an oil well model as described in Example 3, 4, 5 and 6. LH4:18 was positive in the oil release test and was further studied by sandpack column testing.

Example 3

Mini Sandpacks

Three continuous flow oil release tests were done as described above to illustrate the oil release ability of strain LH4:18. One mini sandpack was run as an uninoculated control. The second and third mini sandpacks were identical tests inoculated with strain LH4:18.

After setup, the three mini sandpacks were flooded with a synthetic brine without nitrate (Table 5) at a rate of 0.5 ml/min for 6.6 pore volumes. At that point, the flooding was stopped. The height of the oil in the stand legs was measured, and the amount of oil released relative to the original amount added was calculated. At this point oil release from mini sandpacks #1, 2, and 3 was determined at 25%, 20% and 25%, respectively.

The sandpacks were then either inoculated with cells or just sterile medium as the "control". Mini sandpack #1 was inoculated with the medium (Table 5) that did not contain nitrate. Mini sandpacks #2 and #3 were inoculated with strain LH4:18 at about $10^8$ cfu/ml for 0.3 pore volume, followed by an 0.3 pore volume of nitrate augmented medium (Table 5). All flows were stopped and the wells with the medium with or without inoculum were allowed to incubate for 13 days. After 13 days, nitrate augmented medium was pumped onto the mini sandpacks at a rate of 0.5 ml/hr for an additional 10 pore volumes when the height of the oil in the stand legs was measured and the amount of oil released relative to the original amount added was calculated. In mini sandpack #1 (the uninoculated control), 30% of the original oil had been released while in inoculated mini sandpacks #2 and #3, 37% and 44% of the original oil had been released, respectively (FIG. 5). These observations demonstrated the ability of LH4:18 to facilitate release of significant amounts of oil in a flow through system.

TABLE 5

MEDIUM COMPOSITION
For preinoculation and control flooding, the formulation below without $NaNO_3$ was utilized.

| chemical | amount/liter |
|---|---|
| new trace metals (SL-10) from Table I | 1 mL |
| vitamin solution from Table I | 1 mL |
| Selenite-tungstate solution from Table I | 1 mL |
| $CaCl_2 \cdot 2H_2O$ | 60 mg |
| $MgCl_2 \cdot 6H_2O$ | 270 mg |
| $MgSO_4 \cdot 7H_2O$ | 80 mg |
| KCl | 400 mg |
| $NaH_2PO_4$ | 40 mg |
| $NH_4Cl$ | 500 mg |
| $NaHCO_3$ | 2 g |
| $NaNO_3$ | 1.6 g |
| NaCl | 10 g |

Example 4

Mini Sandpacks with Mixed Inocula

Six continuous flow oil release tests were done as described above to illustrate the oil release ability of strain LH4:18 in combination with a second isolated strain LH4:15. Strain LH4:15 is described in the commonly owned, co-filed, and co-pending application U.S. Ser. No. 12/105,769, and was identified as *Pseudomonas stutzeri* based on its 16S rDNA sequence analysis. This strain represents a predominant species found in typical reservoir injection waters from the North Slope. Three mini sandpacks were used as uninoculated controls while another three columns were identically inoculated tests using a mixture of LH4:18 and LH4:15 as the inoculum.

The six mini sandpacks were flooded with a synthetic brine 1 (Table 6), at a rate of 3.0 ml/min for 6.6 pore volumes after which the flooding was stopped. The height of the oil in the stand legs was measured and the amount of oil released relative to the original amount added was calculated.

The sandpacks were then either inoculated with cells of LH4:15 plus LH4:18 (as described below) or with live injection water from the same Alaskan North Slope field that the oil was obtained from as a control. Three mini sandpacks were inoculated with a mixture of LH4:18 and LH4:15. Each concentrated pure strain was diluted with filter sterilized injection water from the North Slope of Alaska to an optical density measured at 600 nm ($OD_{600}$) of 0.5. Equal volumes of these two diluted pure strains were combined, and the medium was augmented with 1.6 g/l of sodium nitrate. This mixture was pumped into three of the mini sandpack columns for 0.92 pore volume. The three control mini sandpacks were inoculated with 0.92 pore volumes of live injection water from the North Slope of Alaska that had been augmented with 1.6 g/l of sodium nitrate. All flows were stopped and all six wells were allowed to sit for 19 days. At the end of the 19 days, brine 2 (Table 6) was pumped onto the mini sandpacks at a rate of 3.0 ml/hr for an additional 6.6 pore volumes. Periodically, the height of the oil in the stand legs was measured, and the amount of oil released relative to the original amount added was calculated. The average and the maximum additional oil released after inoculation were calculated, and the results are shown in FIG. 6. These results demonstrated the ability of LH4:18 to facilitate release of significant additional oil in a flow through experiment when combined with isolate LH4:15.

TABLE 6

COMPONENTS OF BRINE FOR MINI
SANDPACK EXPERIMENTS IN EXAMPLE 4

| Component | Brine 1 mg/l | Brine 2 mg/l |
|---|---|---|
| NaHCO$_3$ | 1377 | 1377 |
| CaCl$_2$•6H$_2$O | 394 | 394 |
| MgCl$_2$•6H$_2$O | 217 | 217 |
| BaCl$_2$•2H$_2$O | 32 | 32 |
| KCl | 90 | 90 |
| SrCl$_2$•6H$_2$O | 15 | 15 |
| LiCl | 6 | 6 |
| NaCl | 11560 | 11560 |
| NaNO$_3$ | 0 | 400 |

Example 5

Testing for Oil Release in a Sandpack Column

To test the amount of residual oil left in a sandpack after the oil soaked sandpack was flooded with a water solution that simulated the injection brine used in flooding an underground oil reservoir, the sandpack was fabricated as per standard methods described by Abhijit, Y. et al., Supra. A similar core flood/sandpack apparatus and techniques used to operate it are also described by Berry et al., Supra. The use of similar apparatus and techniques for testing microbial treatments in a sandpack is described by Saikrishna M., et al. Supra.

The washed sand was constrained in a Viton® (E.I. du Pont de Nemours & Co., Wilmington, Del.) elastomeric sleeve under a hydraulic pressure of 500 psig. The length of the sandpack was 15.5 cm with diameter 3.8 cm. The sandpack had a pore volume (volume of the sandpack that was empty space) of 70 mL. The following describes calibration of the gamma ray attenuation system. The gamma rays were generated using Americium 241 radioactive source (59.5 KeV). Gamma rays were detected using a common gamma ray detector device, for example a solid state CdTe (cadmium telluride) gamma ray detector XR-100T (Amptek Inc., 14 De Angelo Drive, Bedford, Mass.). Vacuum was pulled on the sandpack, and the gamma ray detector was zeroed to give the absolute minimum gamma ray attenuation with no oil or water on the sandpack. The target oil (with no water present) was then flooded onto the sandpack at a constant flow rate of 80 ml/hr. After more than one pore volume or 70 mL of oil was pumped onto the sandpack, the gamma ray attenuation signal became constant. This gamma ray attenuation signal showed more attenuation due to the presence of the oil. It was used as a calibration point for complete oil saturation (So=1). This oil was removed by a series of solvent flushes that included organic solvents and a final alcohol wash. Vacuum was pulled on the sandpack, and the zero point of gamma ray detector was obtained again. A constant flow of 80 ml/hr of 1.0% sodium iodide doped simulated brine solution (Table 7) was used to saturate the column under vacuum to complete water saturation (Sw=1). Once completely water saturated as indicated by a constant gamma ray attenuation signal, the gamma ray detector was calibrated to this fully water saturated condition. The iodide present in the water causes a substantial attenuation of the gamma ray signal above that of the oil. For two immiscible fluid floodings (oil and simulation brine, Table 7), the gamma ray attenuation signal was used to measure the amount of water saturation (Sw) and oil saturation (So=1−Sw) since the measured attenuation is a linear combination of the attenuation at complete water saturation (Sw=1) and complete oil saturation (So=1). This relationship holds only if there is no gas generated in the sandpack. Consequently, in this experiment, great care was taken to assure any gas that was generated by microbial action or fed into the sandpack remained dissolved by applying a back pressure on the effluent from the sandpack. This back pressure reached as high as 200 psig but was substantially less than the hydraulic constraining pressure on the Viton® sleeve. During these flooding operations with oil and then water, the sandpack differential pressure was measured and used to determine the permeability of the sandpack to oil and to water.

After the gamma ray attenuation signal was calibrated, and the sandpack was at complete water saturation (Sw=1), the crude oil (the same oil used in the other examples) was flooded onto the column at a rate of 400 ml/hr for 10 pore volumes at which point only oil was being produced in the effluent from the sandpack. The gamma ray attenuation signal gave a measure of the initial water saturation (Swi) which was about 0.11%, or 11% of the void volume. During flooding, the differential pressure was measured and used to determine the permeability of the sandpack. The flow of oil onto the sandpack was stopped and the sandpack was aged in contact with the crude oil for one week. After this aging period, the sodium iodide doped brine solution was pumped at a rate of 80 ml/hr for a total of 10 pore volumes after which the gamma ray detector indicated that the residual oil saturation (Sor1) was 0.2%, or 20% of the pore volume. The sandpack was shut in for a 2-week period to mimic the shut in period used for microbial growth in the inoculated sandpack test described in Example 6. After this 2-week shut in period, water flooding (at 80 ml/hr) with the brine solution was continued for another 10 pore volumes. At the end of this flooding, the gamma ray detector indicated that the residual oil saturation (Sor2) had declined to 0.16%, or 16% of a pore volume, indicating that an additional 4% of a pore volume of oil was produced after this control shut in period.

TABLE 7

SIMULATED BRINE COMPOSITION FOR
CONSTRICTED SANDPACK TESTS

| Component | Initial & post shut-in brine composition (g/l) |
|---|---|
| CaCL$_2$•2H$_2$O | 0.10 |
| BaCl$_2$•2H$_2$0 | 0.04 |
| SrCl$_2$•6H$_2$O | 0.06 |
| LiCl | 0.01 |
| NaCl | 6.93 |
| NaI | 10.00 |
| MgCl$_2$•6H$_2$O | 0.12 |
| NaHCO$_3$ | 0.000275 |
| NaNO$_3$ | 1.6 |

Example 6

Testing for Oil Release in a Sandpak Column Following Microbial Actions

The purpose of this example was to test if the addition of strain LH4:18 increased the amount of oil recovered from the sandpack and if there were other effects, specifically loss of permeability within the sandpack that could lead to improved sweep efficiency by biofilm formation in the more permeable zones of the oil reservoir. The sandpack used in Example 5, was reflooded with oil at 400 ml/hr for approximately 15 pore volumes at which point no more oil was produced from the sandpack. The gamma ray detector was used to get an indication of the Swi. The sodium iodide doped brine solution was then pumped into the column at a rate of 80 ml/hr for 10 pore volumes. At this point the permeability was measured as 1.4 darcies and the residual water saturation was 79% of a pore volume. The sandpack was inoculated with 2.8 pore volumes of the LH4:18 culture at a cell density of about $10^7$ cfu/ml in the same brine solution used to flood the column. The culture had been grown using additional nutrients to augment the brine solution (Table 7), specifically, the vitamin, trace elements, and Se/W mixture described in Table 2; 1200 ppm nitrate as sodium nitrate; and 0.5% peptone as the carbon source.

Post inoculation, the sandpack was shut in for a 2-week period to allow for growth of the microbes in the sandpack. After the 2-week shut in period, the brine solution was used to continue the water flooding for another 10 pore volumes at 80 ml/hr. At the end of this flooding, the gamma ray detector indicated that the residual water saturation was 86% of a pore volume and permeability had decreased to 1.1 darcies.

In comparison to the results presented in Example 5, the microbe treated sandpack yielded an additional 2% oil release and decreased the permeability of the sandpack by about 25%. The decrease in permeability was significant given that this was such a high permeability sandpack and implies formation of beneficial biofilms. These biofilms are of great benefit in a heterogeneous formation rock in that biofilm formation could serve to plug the more permeable zones and thus reroute water through less permeable zones thereby forcing more oil out of these zones in a real heterogeneous formation rock.

Example 7

Riboprinting to Determine Species Uniqueness

The 16S rDNA sequence used to determine taxonomy of isolate LH4:18 was 100% homologous to a previously isolated species of *Shewanella putrefaciens* (ATCC BAA453). In order to determine that *Shewanella putrefaciens* strain LH4:18 was a novel isolate, several *Shewanella putrefaciens* were obtained from ATCC, and their 16S and 23 rDNA genes were analyzed by riboprinter as described above. These strains were: *Shewanella putrefaciens* ATCC 8071 (Validation list no. 20. *Int. J. Syst. Bacteriol.* 36, 354-356, 1986); *Shewanella putrefaciens* ATCC BAA453 (Stapleton Jr., R. D., et al., *Aquat. Microb. Ecol.* 38, 81-91, 2005); *Shewanella putrefaciens* ATCC 51753 (Picardal F W, et al. *Appl. Environ. Microbiol.* 59, 3763-3770, 1993). Strain ATCC BAA453 contains two of eight 16S rDNA gene sequences which are 100% homologous to the 16S rDNA sequence of *Shewanella putrefaciens* strain LH4:18. However, analysis performed using the riboprinter protocol (FIG. 7) clearly indicated that the pattern of the EcoRI restriction fragments which hybridize to 16S and 23S rDNA probes was substantially different in LH4:18 compared to BAA453. In addition, the LH4:18 fragment pattern was also substantially different from the other *Shewanella putrefaciens* strains tested. These analyses confirmed that the genomic sequences surrounding the 16S and 23 rDNA genes in strain LH4:18 are substantially different compared to other tested *Shewanella putrefaciens* strains and confirmed the uniqueness of *Shewanella putrefaciens* strain LH4:18.

---

The invention claimed is:

1. An isolated microorganism designated as bacterial *Shewanella putrefaciens* LH4:18 (ATCC No. PTA-8822).

2. An oil recovery enhancing composition comprising:
    a) *Shewanella putrefaciens* LH4:18 (ATCC No. PTA-8822);
    b) one or more electron acceptors; and
    c) at least one carbon source.

3. The composition of claim 2, further comprising one or more additional microorganisms.

4. The composition of claim 3, wherein said one or more additional microorganisms are capable of growing on oil under denitrifying conditions.

5. The composition of claim 4, wherein said one or more additional microorganisms comprises the bacterial isolate *Pseudomonas stutzeri* LH4:15 (ATCC No. PTA-8823).

6. The composition of claim 2, wherein said at least one carbon source comprises oil or an oil component.

7. A method for improving oil recovery from an oil reservoir comprising:
    a) providing a composition comprising as bacterial isolate *Shewanella putrefaciens* LH4:18 (ATCC No. PTA-8822), and minimal medium comprising simple nitrates capable of promoting the growth of said isolate; and
    b) inoculating said reservoir with the composition of (a);
    wherein growth of said isolate, under denitrifying conditions, in the oil reservoir promotes improved oil recovery.

8. The method of claim 7, wherein the composition of (a) further comprises one or more additional microorganisms capable of growing on oil under denitrifying conditions.

9. The method of claim 8, wherein said one or more additional microorganisms comprises the bacterial isolate *Pseudomonas stutzeri* LH4:15 (ATCC No. PTA-8823).

10. The method of claim 7, wherein oil recovery is improved by growth of bacterial isolate *Shewanella putrefaciens* LH4:18 (ATCC No. PTA-8822) resulting in one or more of the following: (1) alteration of the permeability of the subterranean formation to improve water sweep efficiency; (2) production of biosurfactants which decrease surface and interfacial tensions; (3) mediation of changes in wettability; (4) production of polymers which facilitate mobility of petroleum; (5) generation of gases that increase formation pressure; and (6) reduction of oil viscosity.

11. The method of claim 10, wherein the gases of (5) comprise $CO_2$.

12. A method for promoting hydrocarbon bioremediation comprising applying bacterial isolate *Shewanella putrefaciens* LH4:18 (ATCC No. PTA-8822) to an area contaminated with hydrocarbons.

13. The method of claim 12, further comprising applying one or more additional microorganism.

14. The method of claim 13, wherein said one or more additional microorganisms comprises the bacterial isolate *Pseudomonas stutzeri* LH4:15 (ATCC No. PTA-8823).

15. A method for promoting oil pipeline maintenance comprising applying bacterial isolate *Shewanella putrefaciens* LH4:18 (ATCC No. PTA-8822) to an oil pipeline.

16. The method of claim 15, further comprising applying one or more additional microorganisms to said pipeline.

17. The method of claim 16, wherein said one or more additional microorganisms comprises the bacterial isolate *Pseudomonas stutzeri* LH4:15 (ATCC No. PTA-8823).

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: artificial sequence
<220> FEATURE:
<223> OTHER INFORMATION: primer 1492R

<400> SEQUENCE: 1
cggttacctt gttacgactt                    20

<210> SEQ ID NO 2
<211> LENGTH: 20
<212> TYPE: DNA
<213> ORGANISM: artificial sequence
<220> FEATURE:
<223> OTHER INFORMATION: primer 8F

<400> SEQUENCE: 2
agagtttgat ymtggctcag                    20